United States Patent [19]

Giesy et al.

[11] Patent Number: 4,798,193
[45] Date of Patent: Jan. 17, 1989

[54] PROTECTIVE SHEATH INSTRUMENT CARRIER

[75] Inventors: Jerry D. Giesy, Portland, Oreg.; George D. Hermann, Palo Alto, Calif.; Matthew W. Hoskins, Beaverton, Oreg.

[73] Assignee: Thomas J. Fogarty, Palo Alto, Calif.

[21] Appl. No.: 51,862

[22] Filed: May 18, 1987

[51] Int. Cl.⁴ .............................................. A61B 1/06
[52] U.S. Cl. .................................... 128/7; 128/348.1; 128/772; 604/164
[58] Field of Search ............... 604/54, 164, 165, 166, 604/170, 264; 128/772, 656, 657, 658, 341, 343, 4.7, 348.1

[56] References Cited

U.S. PATENT DOCUMENTS

| | | | |
|---|---|---|---|
| 2,120,996 | 6/1938 | Wappler | 128/7 |
| 2,657,691 | 11/1953 | Nordstom, Jr. | 128/303 R |
| 2,936,760 | 5/1960 | Gants | 604/102 |
| 3,766,924 | 10/1973 | Pidgeon . | |
| 3,804,097 | 4/1974 | Rudie . | |
| 3,867,945 | 2/1975 | Long . | |
| 4,027,668 | 5/1977 | Dunn . | |
| 4,195,637 | 4/1980 | Gruntzig . | |
| 4,485,805 | 12/1984 | Foster, Jr. . | |
| 4,493,711 | 1/1985 | Chin et al. . | |
| 4,545,390 | 10/1985 | Leary | 128/772 |
| 4,619,643 | 10/1986 | Bai | 604/164 |
| 4,686,984 | 8/1987 | Bonnet | 604/343 |

FOREIGN PATENT DOCUMENTS 8603129  6/1986  Fed. Rep. of Germany ........ 604/96

Primary Examiner—Stephen C. Pellegrino
Attorney, Agent, or Firm—Limbach, Limbach & Sutton

[57] ABSTRACT

An open ended tubular sheath is provided with an annular guide element to facilitate placement of the sheath within a body passage. In use a guide wire is directed into the passage and the guide element is then slid over the wire to direct the sheath into the passage. Once in place, the sheath may be used to direct instruments into the passage without significant abrasion or trauma. The guide element may take the form of a loop or tube. Column strength may be provided to the sheath either by the guide element or a stiffener engaged with the element or the sheath.

15 Claims, 4 Drawing Sheets

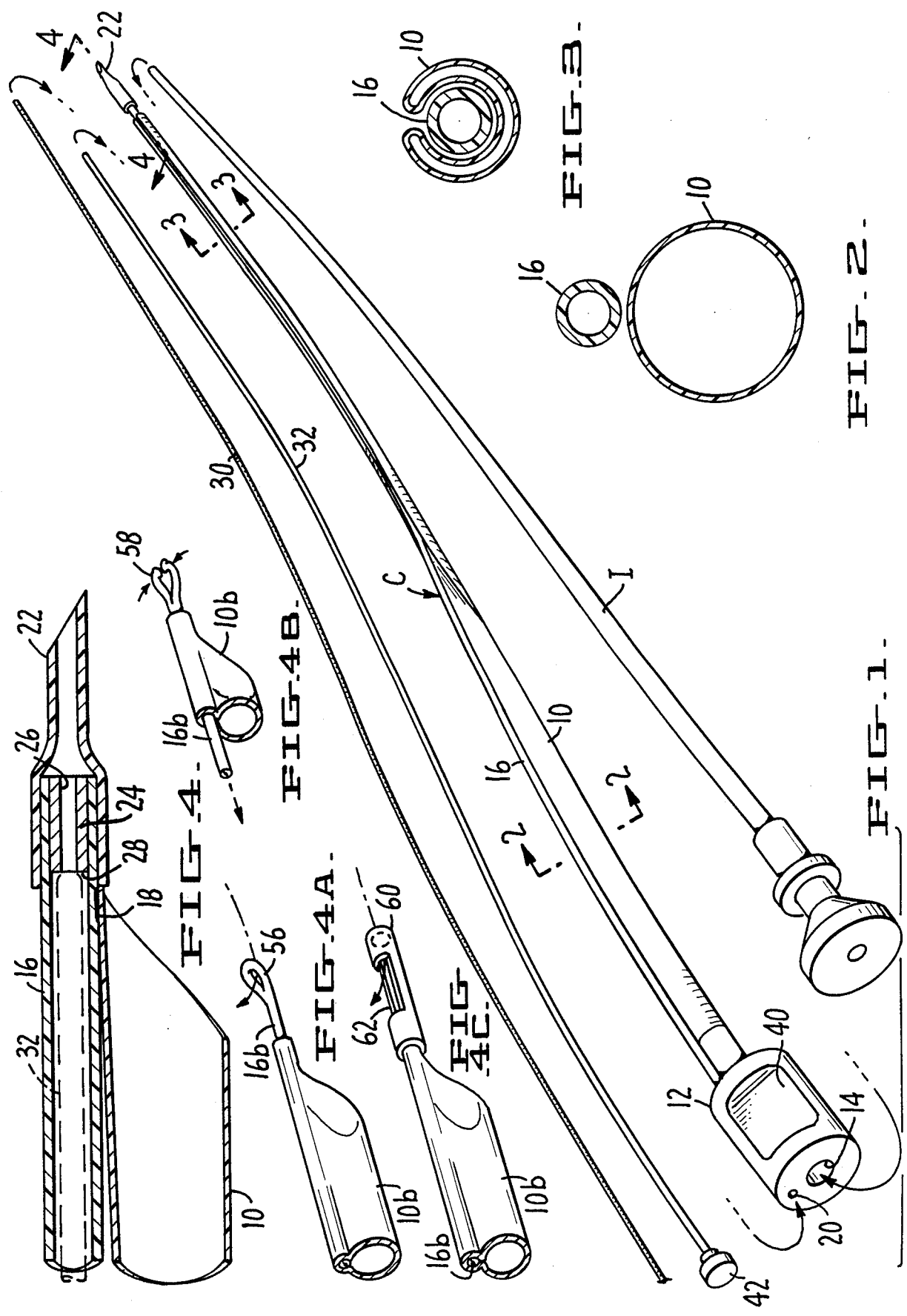

4,798,193

PROTECTIVE SHEATH INSTRUMENT CARRIER

BACKGROUND OF THE INVENTION

The present invention relates to an improved apparatus and method for placing a flexible tubular membrane within a body passage to shield the passage from abrasion by an instrument which is later passed through the membrane.

The invention is particularly concerned with such a membrane or sheath which may be used to accommodate the passage of instruments into delicate body passages for diagnostic or therapeutic purposes. The passages ay take the form of open body passages, such as the urethra, or normally closed body passages such as blood vessels and arteries which are entered percutaneously.

In the prior art, various techniques have been used to reduce the friction between a body passage and an instrument introduced into the passage. The most common of these use pre-dilation of the passage and/or lubrication of the instrument. Although these reduce friction between the instrument and the walls of the body passage, they do not eliminate it. Another technique is to line the body passage with a membrane or sheath which shields the passage from the instrument. With this technique, the instrument is passed through the sheath and friction between the body passage and the instrument is eliminated. U.S. Pat. No. 4,493,711 discloses a TUBULAR EXTRUSION CATHETER which provides such a membrane or sheath.

SUMMARY OF THE INVENTION

The present invention is concerned with an improved apparatus and method which provides a sheath which may be guided into place within a body passage over a guide wire. In its more particular aspects, it is concerned with such a sheath which is very flexible and thin and may be directed into place in a collapsed condition and, once in place, expanded in response to the passage of an instrument therethrough. Unique column strength imparting means are provided both to facilitate initial guidance of the sheath and to place and facilitate removal of an instrument from the sheath after the therapeutic or diagnostic function of the instrument is complete.

A principal object of the invention is to provide an improved apparatus and method for placing a protective sheath within a body passage.

Another object of the invention is to provide such an apparatus and method which enables the sheath to be directed into place over a pre-positioned guide wire located within the body passage.

A further object of the invention is to provide such an apparatus and method wherein the sheath comprises a very thin flexible membrane and column strength may be imparted to the sheath both to facilitate its placement and the removal of an instrument therefrom.

Still another object of the invention is to provide such an apparatus and method wherein the sheath is very flexible and may readily bend during placement to facilitate its movement through tortuous body passages.

Still another object of the invention is to provide such a sheath which may be extended into place through a cystoscope and, once in place, facilitates removal of the cystoscope therefrom, while the sheath remains within a body passage.

Yet a further object of the invention is to provide such a sheath with a handle which may be used to facilitate its placement and removal.

Yet another object related to the latter object is to provide such a handle which may be removed to enable the sheath to pass through an instrument, such as a cystoscope.

Another object of the invention is to provide such a sheath with guide wire accommodating means which does not restrict the interior of the sheath.

These and other objects will become more apparent when viewed in light of the accompanying drawings and following detailed description.

BRIEF DESCRIPTION OF THE DRAWINGS

FIG. 1 is a perspective view of a first embodiment of the instrument carrier or sheath, illustrating in exploded fashion the sheath, a guide wire and stiffening stylet used with the sheath, and an instrument which may be extended into the sheath;

FIGS. 2, 3, and 4 are cross-sectional views taken on the planes designated by lines 2—2, 3—3, and 4—4, respectively, of FIG. 1;

FIGS. 4A, 4B and 4C are perspective views, with parts thereof broken away, illustrating alternative guide wire accommodating structures which may be secured to the tip of the sheath;

DESCRIPTION OF THE PREFERRED EMBODIMENTS

Figure 5:
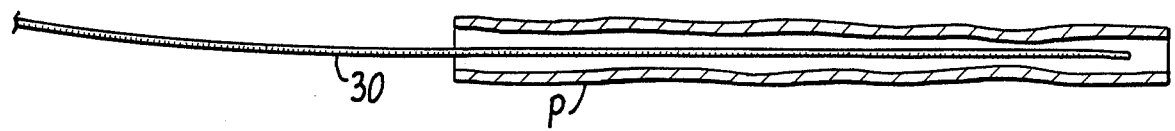
FIGS. 5–12 sequentially illustrate the method of placing the first embodiment sheath within a body passage, utilizing the sheath for placement and removal of an instrument, and removing the sheath from the passage.

Referring now to FIG. 1, the first embodiment instrument carrier therein is designated in its entirety by the letter "C". This carrier comprises an open-ended tubular sheath 10 having its proximal end secured to a handle 12 with an opening 14 communicating with the interior of the sheath. A catheter 16 extends longitudinally to one side of the sheath 10 and is secured to the distal end of the sheath by an adhered connection 18, as may be seen in FIG. 4. The proximal end of the catheter 16 communicates with an opening 20 extending through the handle 12.

The end of the catheter 16 carries a flexible tip 22 which extends forwardly therefrom and facilitates movement of the carrier through a body passage. A reduced diameter bushing 24 is fixedly received within the distal end of the catheter 16. This bushing provides a reduced diameter bore 26 for the slidable accommodation of a guide wire, and a shoulder 28 for abutment with the end of a stylet. The guide wire and stylet are illustrated in FIG. 1 and designated by the numerals 30 and 32, respectively. Their operation will become more apparent from the following discussion. The stylet 32 may also be seen in phantom lines in FIG. 4.

FIG. 1 also shows an instrument "I" which may be placed within a body passage through means of the carrier "C". The instrument "I" is for illustrative purposes only and forms no part of the inventive apparatus. As shown, it takes the form of an optical instrument proportioned for passage into the opening 14 and through the sheath 10.

FIGS. 5-12 illustrate the first embodiment carrier "C" in the process of being used in a body passage "P". The passage may be literally any passage within the human body, such as an artery or vein. Although not illustrated, it should be understood that if it is such a closed passage, entry therein could be percutaneously achieved.

Figure 6:
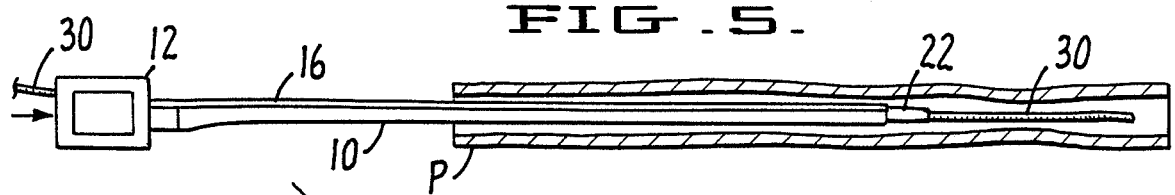

The first step of the sequence is shown in FIG. 5. There, the guide wire 30 is shown being directed into the body passage "P". This would be achieved in conventional manner to extend the wire through the passage and the area where diagnosis or treatment is desired. Once the wire is in place, the catheter 16 is threaded over the wire and into the body passage, as shown in FIG. 6. This is achieved with the sheath 10 in a fully collapsed condition (See FIG. 3) and manually facilitated through means of the handle 12. It should be appreciated that the wire extends slidably through the catheter 16 and the opening 20 in the handle 12.

Figure 7:
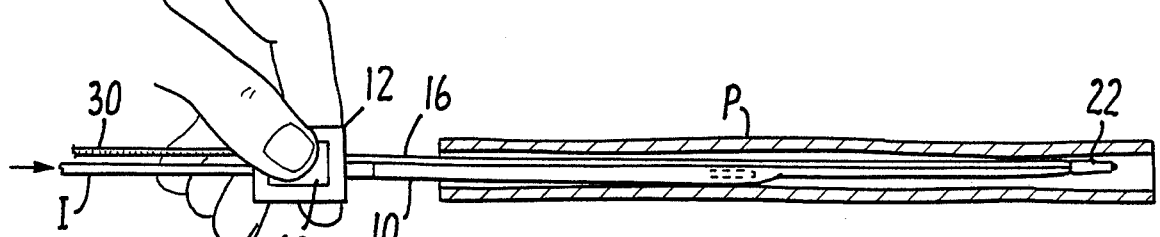
Figure 8:
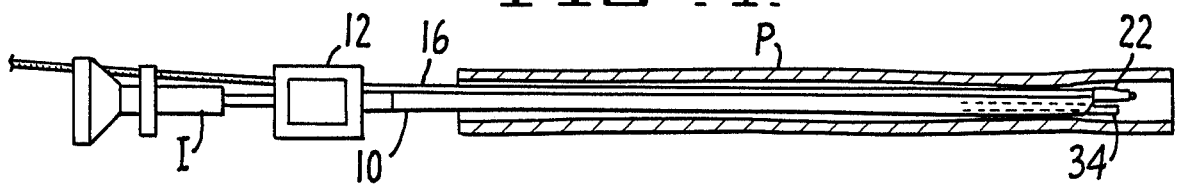
Figure 9:
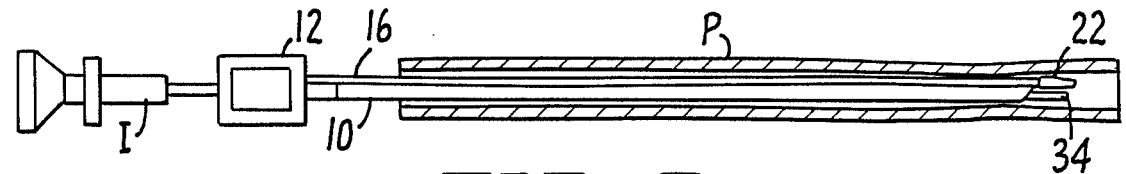

Once the carrier "C" is fully in place, as shown in FIG. 7, the instrument "I" is introduced into the sheath 10 through the handle 12, as shown in FIG. 7, and fed into place within the passage "P". During the course of the latter operation, the handle 12 is gripped as the instrument is fed through the opening 14. FIG. 8 shows the instrument fully in place within the passage "P", with the distal end of the instrument, designated 34, extending from the open distal end of the sheath 10. In the latter condition, the illustrative optical instrument "I" may be used to view the interior of the passage "P".

Figure 10:
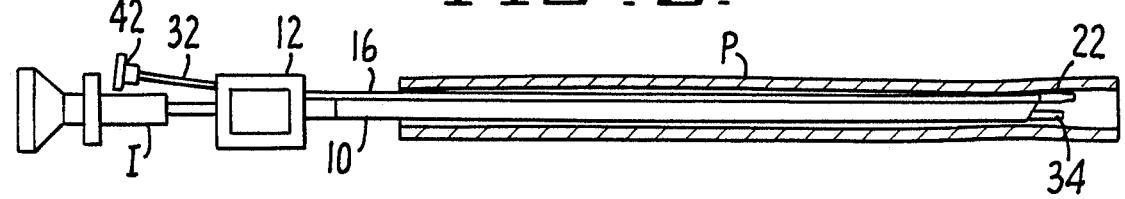

FIGS. 9-12 show the process of removing the instrument and sheath from the passage "P". There it will be seen in FIG. 9 that the guide wire 30 has been removed and, in FIG. 10, that the stylet 32 has been inserted into the catheter 16 through the opening 20. When fully extended into the catheter 16, as shown in FIG. 10, the distal end of the stylet 32 abuts against the shoulder 28 of the bushing 24, as shown by the phantom line representation of FIG. 4. Thus, the stylet functions to impart column strength to the sheath 10 and holds the sheath against collapse as the instrument "I" is withdrawn therefrom.

Figure 11:
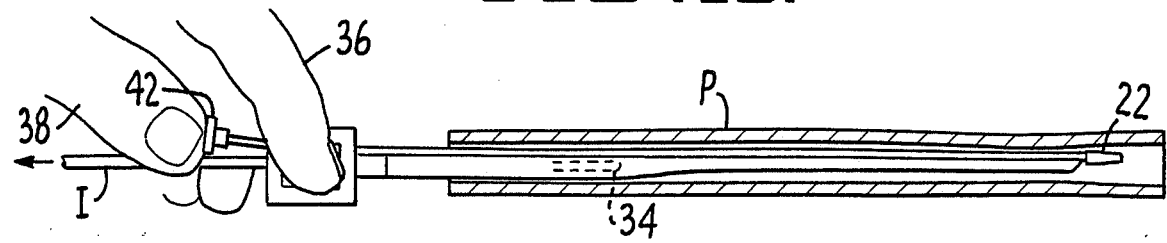

FIG. 11 shows the instrument "I" being withdrawn from the sheath 10, as the handle 12 and proximal end of the stylet 32 are held by the human hand of the user. The fingers and thumb of the hand are designated by the numerals 36 and 38. Gripping of the handle and stylet is facilitated by finger grooves 40 formed in the outside surface of the handle 30 and a knob 42 secured to the proximal end of the stylet 30.

Figure 12:
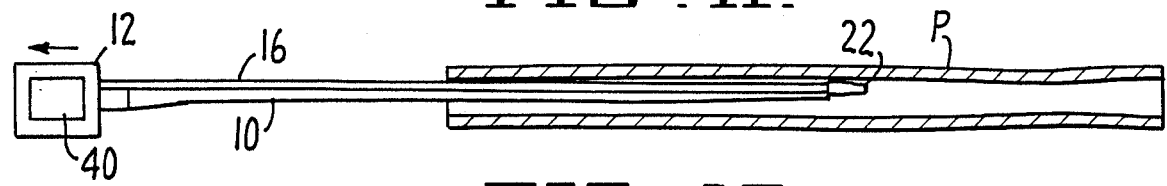

The final step of removal is shown in FIG. 12. There the instrument has been fully removed from the sheath 10 and the carrier "C" is shown being withdrawn from the passage "P". As shown, the stylet 32 has been withdrawn prior to withdrawal of the carrier from the passage. If desired, the stylet might be left in place during withdrawal of the carrier.

While in no way intended to be limiting, it is noted that an exemplary embodiment of the carrier "C" might be characterized as follows:

| Element | Characteristics of the Element |
| --- | --- |
| sheath 10 | polyethylene, .007 inches thick, 14 French diameter, 15 inches length |
| guide wire 30 | flexible stainless steel, 2 French diameter, length 20-30 inches |
| catheter 16 | polyethylene or nylon, 6 French outside diameter, 4.5 French inside diameter, length 15 inches |
| bushing 24 | stainless steel, 3 French bore diameter |
| stylet | stainless steel, 4 French diameter, 18 inches in length |

It should be understood that these characteristics and dimensions may vary, depending upon the body passage to be traversed. While they are referred to with respect to the first embodiment, they may also apply, as appropriate, to the second and third embodiments.

The apparatus of the second embodiment, as shown in FIGS. 13-18, corresponds to that of the first embodiment, with the exception that:

1. The catheter, designated 16a, is secured interiorly of the sheath designated 10a and bonded to the sheath over its entire length;

2. The sheath 10a has an open mouth 44 at its proximal end; and

3. The handle, designated 12a comprises a collet which may be clamped to or released from the catheter 16a.

Figure 13:
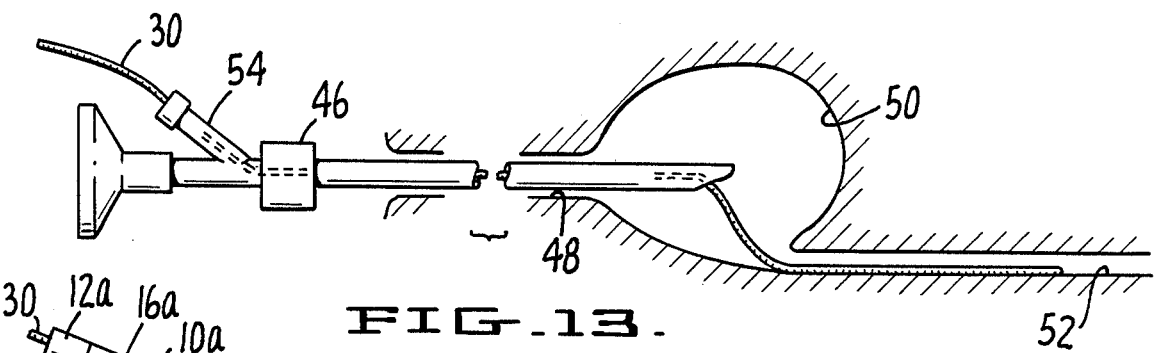
FIGS. 13–17 sequentially illustrate the method of placing a second embodiment of the sheath within the ureter through means of a cystoscope, and utilizing the sheath for the passage of an instrument into the ureter.
Figure 14:
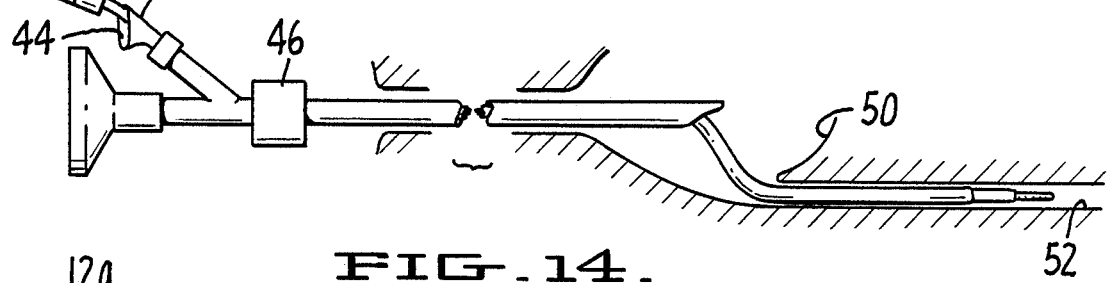
Figure 15:
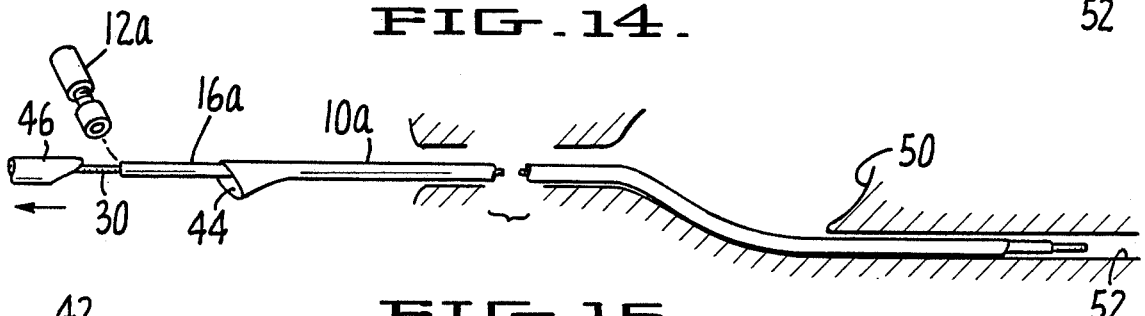

The operation of the second embodiment is generally the same as that of the first embodiment, with the exception that the collet may be removed to facilitate passage of the instrument carrier through the body of an instrument. Such an instrument is shown in FIGS. 13-15 as a cystoscope 46. As there shown, the cystoscope is being used to direct the carrier into the ureter. The body passage in FIG. 13 comprises urethra 48, bladder 50 and ureter 52.

In the sequence shown in FIGS. 13-14, the cystoscope is first introduced into the urethra and passed into the bladder 50. Then, the guide wire 30 is passed into the cystoscope through a Y-branch 54 at its proximal end. Using the cystoscope for visual observation, the wire is fed through the cystoscope and into the bladder and then directed into the ureter 52. FIG. 13 shows the wire in the latter condition.

Figure 16:
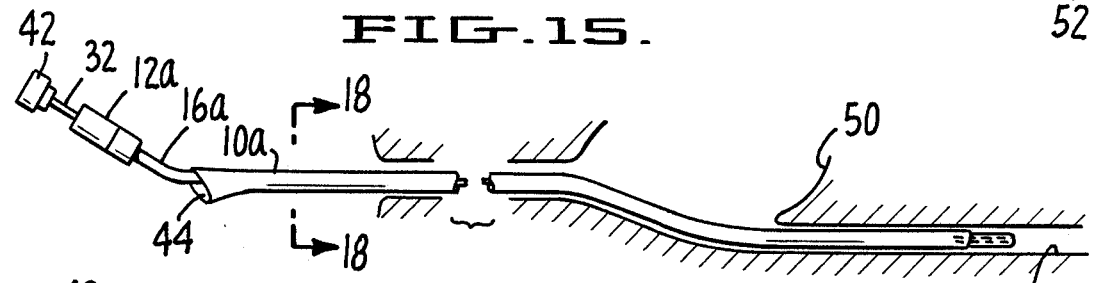
Figure 17:
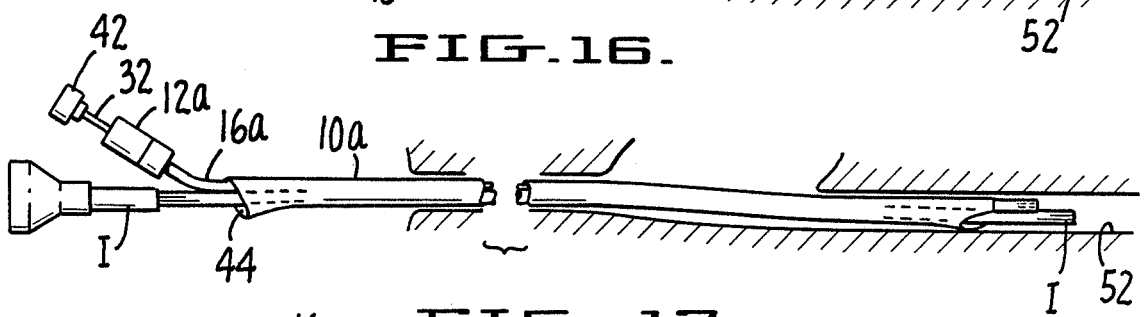

Once the guide wire is in place within the ureter, as shown in FIG. 13, the catheter 16a is threaded over the wire and the carrier is then forced through the Y-branch 54 and into the ureter, as shown in FIG. 14. Thereafter, the collet 12a is removed from the catheter 16a, as shown in FIG. 15, and the cystoscope 46 is withdrawn,.leaving the instrument carrier in place. The collet is then reattached to the catheter 16a and the stylet 32 is passed through the catheter as shown in FIG. 16. This functions to somewhat stiffen and straighten the sheath 10a. Thereafter, instrument "I" may be introduced into the sheath through the mouth 44 and directed into the ureter, as shown in FIG. 17.

Removal of the instrument and carrier of the second embodiment is carried out by steps corresponding to those of FIGS. 11 and 12 of the first embodiment, namely, the instrument "I" is withdrawn from the carrier, while the stylet and proximal end of the carrier are held through means of the knob 42 and collet 12a. Once the instrument is removed, the entire carrier may be removed, preferably by first removing the stylet 32 and then by removing the sheath 10a with attached catheter 16a.

Figure 18:
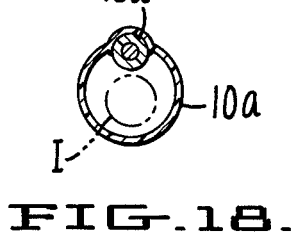
FIG. 18 is a cross-sectional view taken on the plane designated by line 18—18 of FIG. 16.

FIG. 18 illustrates how the catheter 16a is adhered to the interior of the sheath 10a. So adhering the catheter over the full length of the sheath has the advantage that tension forces between the catheter and the sheath are distributed over the entire length of the sheath, rather than concentrated at its distal and proximal end, as they would be in the first embodiment.

The third embodiment, as shown in FIGS. 19–22, differs from the second embodiment in the following respects:

1. A flexible stylet 16b is secured within the sheath 10b in place of the catheter 16a; and
2. An eye 56 is formed on the distal end of the stylet 16b to the outside of the sheath 10b (see FIG. 4A).

Figure 19:
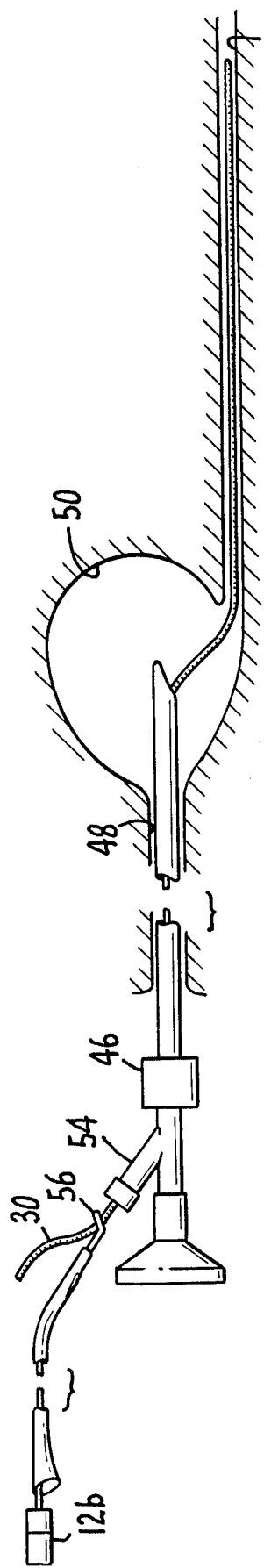
FIGS. 19–21 sequentially illustrate the method of placing a third embodiment of the sheath within the ureter through means of a cystoscope, and utilizing the sheath for the passage of an instrument into the ureter.
Figure 20:
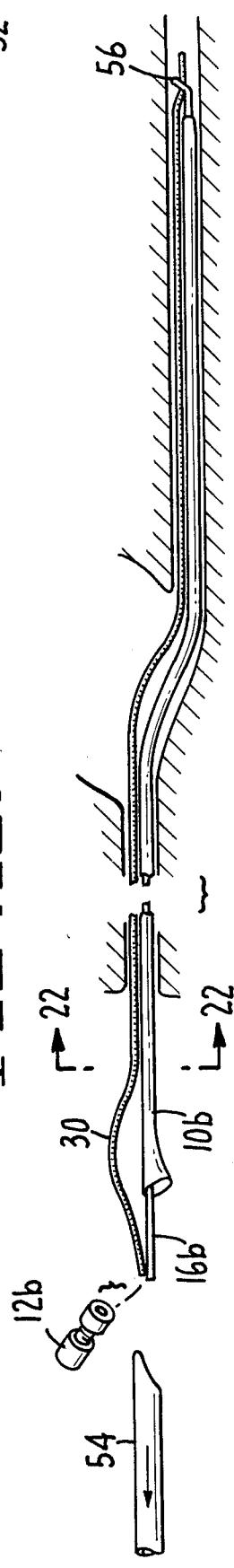
Figure 21:
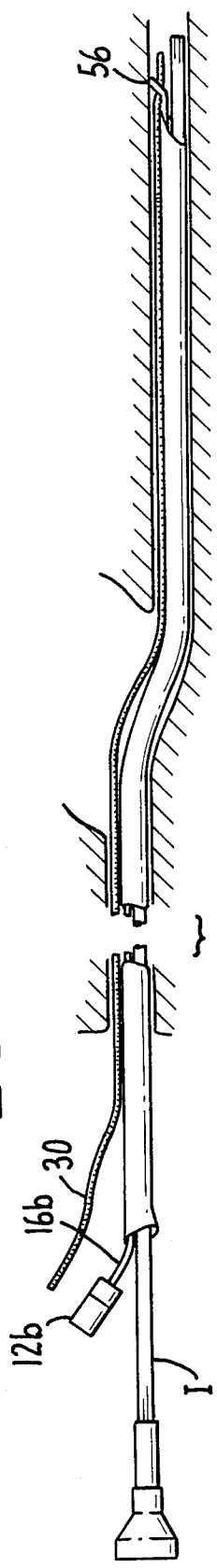

The operation of the third embodiment is similar to that of the second embodiment, with the exception that the carrier is guided into place by sliding the eye 56 over the guide wire 30, rather than by sliding the guide wire through a catheter within the sheath. The third embodiment operation, in the process of inserting the carrier into the ureter, is shown in FIGS. 19–21. There, in FIG. 19, it will be seen that the cystoscope 46 is directed through the urethra and into the bladder and then the guide wire 30 is directed through the cystoscope and into the ureter. With the wire so in place, the carrier is directed into place by sliding the eye 56 over the wire and through the Y-branch 54 of the cystoscope.

Manipulation of the carrier is facilitated by a collet 12b releasably secured to the stylet 16b, as shown in FIG. 19. FIG. 20 shows the collet removed from the stylet after the carrier is fully in place within the ureter, and the cystoscope in the process of being withdrawn. FIG. 21 shows the collet reattached to the stylet 16b and an instrument "I" being passed into the ureter through the sheath 10b.

The process of removing the instrument and the carrier of the third embodiment is essentially the same as that shown in FIGS. 11 and 12 for the first embodiment. Namely, the instrument is withdrawn from the sheath while the sheath is held in place through the stylet 16b and attached collet 12b. Once the instrument is removed, the entire carrier assembly may be withdrawn. If desired, the guide wire 30 may be removed in advance of removal of the carrier assembly.

Figure 22:
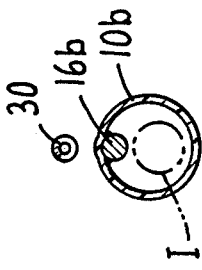
FIG. 22 is a cross-sectional view taken on the plane designated by line 22—22 of FIG. 20.

FIG. 22 shows how the stylet 16b is secured within the sheath 10b. It should be appreciated that the stylet is secured to the sheath over its entire length, thereby imparting column strength to the sheath and distributing any tension forces between the stylet and sheath over the full length of the sheath.

FIGS. 4A, 4B and 4C illustrate three alternative forms which the eye at the end of the stylet 16b may take. The FIG. 4A form is that which has been described with respect to FIGS. 19–21. The FIG. 4B embodiment employs a split-loop which may be open to facilitate snapping of the eye, designated 58 over a guide wire. If desired, the FIG. 4B embodiment may be so constructed that the legs of the loop are drawn toward one another in response to withdrawing the stylet 16b into the sheath 10b. FIG. 4C shows a modified embodiment where the eye, designated 60 takes the form of a cylindrical extension secured to the stylet 16b, with the eye being formed by the open end of the sleeve and a cut-out 62 in the side of the sleeve.

Conclusion

While preferred embodiments of the invention have been illustrated and described, it should be understood that the invention is not intended to be limited to these embodiments, but rather is defined by the accompanying claims.

We claim:

1. A carrier for placing an instrument in a body passage to shield the passage from brasion by the instrument, said carrier comprising: an open ended sheath in the form of a thin flexible membrance collapsible upon itself, said sheath having an interior of a diameter greater than the cross-section of the instrument to be placed; guide wire accommodating means secured to said sheath to enable said sheath to be slid over a guide wire and into place within a body passage and isolate the guide wire from obstructing the passage of an instrument through the interior of the sheath; column strength imparting means operatively associated with the guide wire accommodating means to apply pressure thereto to draw the sheath along a guide wire and into a body passage within which the wire is placed.

2. A carrier according to claim 1 wherein the guide wire accommodating means comprises a loop secured to the sheath adjacent the distal end thereof.

3. A carrier according to claim 2 wherein the column strength imparting means comprises a stylet secured to and extending longitudinally of said sheath.

4. A carrier according to claim 2 further comprising means to selectively split the loop to enable the loop to be disengaged from a guide wire.

5. A carrier according to claim 1 wherein the guide wire accommodating means comprising a flexible tube extending longitudinally of the sheath and secured to the sheath adjacent the distal end thereof.

6. A carrier according to claim 5 wherein the tube provides the column strength imparting means.

7. A carrier according to claim 5 further comprising stiffening means cooperable with the tube to selectively impart additional column strength to the sleeve.

8. A carrier according to claim 7 wherein the stiffening means comprises a reduced diameter collar formed within the tube and a stylet insertable into the tube for abutment with said collar.

9. A method of placing an instrument with a body passage, said method comprising: providing a flexible tubular sheath having an annular guide element adjacent the distal end thereof and an interior of a diameter greater than the cross-section of the instrument; directing a flexible guide wire through the body passage; sliding the guide element over the wire to place the sheath within the body passage; passing the instrument into the sheath.

10. A method according to claim 9 further comprising removing the instrument after placement by steps comprising: withdrawing the guide wire from the body passage; extending a stylet through the body passage and into abutment with the guide element; and withdrawing the instrument from the sheath while maintaining the stylet in abutment with the guide element.

11. A method according to claim 10 further comprising withdrawing the stylet and sheath from the body passage after withdrawal of the instrument.

12. A method of placing an instrument in the ureter, said method comprising; passing a cystoscope through the urethra and into the bladder; extending a guide wire through the cystoscope and bladder and into the ureter;

providing a flexible open ended tubular sheath having an interior of a diameter greater than the cross-section of the instrument to be placed, said sheath having an annular guide element secured adjacent the distal end thereof; sliding the guide element over the guide wire to direct the sheath into the ureter; withdrawing the cystoscope from the bladder and urethra while leaving the guide wire in place; and, passing the instrument through the sheath and into the ureter.

13. A carrier for placing an instrument in a body passage to shield the passage from abrasion by the instrument, said carrier comprising: a flexible open ended sheath having an interior of a diameter greater that the cross-section of the instrument to be placed; a sleeve secured to and extending longitudinally from the distal end of the sheath to form a guide loop defined by connected openings in the side and distal end of said sleeve, said loop being slidable over a guide wire to enable said sheath to be slid over the guide wire and into place within a body passage and isolate the guide wire from obstructing the passage of an instrument through the interior of the sheath; column strength imparting means operatively associated with the loop to apply pressure thereto to draw the sheath along a guide wire and into a body passage within which the wire is placed.

14. A carrier for placing an instrument in a body passage to shield the passage from abrasion by the instrument, said carrier comprising: a flexible open ended sheath having an interior of a diameter greater than the cross-section of the instrument to be placed; guide wire accommodating means secured to said sheath to enable said sheath to be slid over a guide wire and into place within a body passage and isolate the guide wire from obstructing the passage of an instrument through the interior of the sheath; column strength imparting means operatively associated with the guide wire accommodating means to apply pressure thereto to draw the sheath along a guide wire and into a body passage within which the wire is placed; and a handle secured to the proximal end of the sheath to facilitate placement thereof within a body passage.

15. A carrier according to claim 14 wherein the handle comprises a collet releasably clamped to the sheath whereby the handle may be selectively secured to and removed from the sheath.

* * * * *